(12) United States Patent
Eda et al.

(10) Patent No.: US 12,152,807 B2
(45) Date of Patent: Nov. 26, 2024

(54) LIQUID ATOMIZING APPARATUS

(71) Applicant: NORITAKE CO., LIMITED, Nagoya (JP)

(72) Inventors: Tomokazu Eda, Nisshin (JP); Teruhisa Fujii, Nagoya (JP); Hitoshi Kato, Yatomi (JP); Yusuke Shimizu, Kuwana (JP)

(73) Assignee: NORITAKE CO., LIMITED, Nagoya (JP)

( * ) Notice: Subject to any disclaimer, the term of this patent is extended or adjusted under 35 U.S.C. 154(b) by 103 days.

(21) Appl. No.: 16/968,070

(22) PCT Filed: Jan. 18, 2019

(86) PCT No.: PCT/JP2019/001472
§ 371 (c)(1),
(2) Date: Aug. 6, 2020

(87) PCT Pub. No.: WO2019/155851
PCT Pub. Date: Aug. 15, 2019

(65) Prior Publication Data
US 2021/0364176 A1 Nov. 25, 2021

(30) Foreign Application Priority Data

Feb. 12, 2018 (JP) ................................. 2018-022654

(51) Int. Cl.
*F24F 6/04* (2006.01)
*B05B 17/00* (2006.01)

(52) U.S. Cl.
CPC ................ *F24F 6/04* (2013.01); *B05B 17/00* (2013.01)

(58) Field of Classification Search
CPC ........... B05B 17/04; B05B 17/00; B05B 7/32; B05B 7/2483; B05B 7/2491; B05B 12/06;
(Continued)

(56) References Cited

U.S. PATENT DOCUMENTS

| 654,725 A | * | 7/1900 | Savostyanov | ............. F24F 6/04 261/103 |
| 684,217 A | * | 10/1901 | Gardner | .................... F24F 6/04 261/103 |

(Continued)

FOREIGN PATENT DOCUMENTS

| DE | 4319387 C1 | * | 7/1994 | ................ B01D 1/00 |
| EP | 175601 A | * | 3/1986 | ............. C30B 25/14 |

(Continued)

OTHER PUBLICATIONS

JPS61125368 translation (Year: 1986).*
(Continued)

*Primary Examiner* — Stephen Hobson
(74) *Attorney, Agent, or Firm* — Oliff PLC

(57) ABSTRACT

A liquid atomizing apparatus includes: an atomizing body member made of a porous body having micropores connected in a three-dimensional network, the atomizing body member having a surface including a part serving as a gas pressurized-inflow surface and another part serving as a gas release surface; a liquid supply unit for supplying a liquid to the atomizing body member, the liquid being to be impregnated into the micropores of the atomizing body member; and a gas supply unit for setting gas pressure on the gas pressurized-inflow surface of the atomizing body member to be higher than on the gas release surface of the atomizing body member and injecting the gas into the micropores of the atomizing body member through the gas pressurized-inflow surface, and releasing a mist of the liquid having been impregnated in the micropores together with the gas from the gas release surface.

4 Claims, 4 Drawing Sheets

(58) Field of Classification Search
CPC ....... F24F 6/00; F24F 6/12; F24F 6/04; A61H 33/12; A61M 11/04
See application file for complete search history.

(56) References Cited

U.S. PATENT DOCUMENTS

| | | | | |
|---|---|---|---|---|
| 1,283,950 | A * | 11/1918 | Stiefel | F24F 6/04 261/103 |
| 1,994,523 | A * | 3/1935 | Kohut | F24F 6/04 261/24 |
| 2,099,009 | A * | 11/1937 | Finley | F24D 19/0082 237/78 B |
| 2,161,834 | A * | 6/1939 | Seeley | F24D 19/0082 96/299 |
| 2,326,089 | A * | 8/1943 | Wittman | F24D 19/0082 261/103 |
| 3,427,005 | A * | 2/1969 | Kuykendall | F25B 39/04 62/305 |
| 3,722,838 | A * | 3/1973 | Swimmer | F24F 6/04 261/100 |
| 3,757,494 | A * | 9/1973 | Keuls | F24F 3/12 261/99 |
| 3,834,683 | A * | 9/1974 | McDuffee | F24F 3/14 261/138 |
| 4,029,723 | A * | 6/1977 | Morrison | F24F 6/04 261/103 |
| 4,063,899 | A * | 12/1977 | Cheron | B01D 53/62 261/99 |
| 4,237,080 | A * | 12/1980 | Elliott | F24F 6/06 261/80 |
| 4,389,352 | A * | 6/1983 | Bohanon, Sr. | F24F 6/04 261/106 |
| 4,706,552 | A * | 11/1987 | Maguire | F24F 6/043 454/291 |
| 5,324,230 | A * | 6/1994 | Hist | F24F 6/043 454/328 |
| 5,624,610 | A * | 4/1997 | Yokoya | F24F 3/1417 261/104 |
| 5,711,816 | A * | 1/1998 | Kirlin | C23C 16/4481 261/DIG. 65 |
| 5,882,416 | A * | 3/1999 | Van Buskirk | C23C 16/448 261/106 |
| 6,175,687 | B1 * | 1/2001 | Imamura | F24F 6/043 392/397 |
| 6,474,628 | B1 * | 11/2002 | Stroh | F24F 6/04 261/99 |
| 6,850,698 | B1 * | 2/2005 | Goh | F24F 6/043 392/395 |
| 7,805,953 | B2 * | 10/2010 | Jensen | F24F 8/10 62/506 |
| 7,975,993 | B2 * | 7/2011 | Ono | C23C 16/4486 261/DIG. 65 |
| 8,162,298 | B2 * | 4/2012 | Ono | C23C 16/4486 261/DIG. 65 |
| 8,628,621 | B2 * | 1/2014 | Lee | C23C 14/12 118/724 |
| 8,683,817 | B2 * | 4/2014 | Fraser | F25B 49/027 62/428 |
| 8,833,740 | B2 * | 9/2014 | Ha | F24F 6/043 261/154 |
| 9,005,365 | B2 * | 4/2015 | Bulovic | C23C 16/448 118/721 |
| 9,079,146 | B2 * | 7/2015 | Wallace | C01B 3/065 |
| 9,358,569 | B2 * | 6/2016 | Burt | B05B 17/0615 |
| 9,816,715 | B2 * | 11/2017 | Morikawa | F24F 6/02 |
| 9,942,946 | B2 * | 4/2018 | Long | C23C 16/45565 |
| 9,957,612 | B2 * | 5/2018 | Woelk | B01D 1/14 |
| 9,987,456 | B2 * | 6/2018 | Lee | A61M 16/1045 |
| 10,228,150 | B2 * | 3/2019 | Lee | F24F 6/04 |
| 10,294,584 | B2 * | 5/2019 | Gupta | C30B 29/36 |
| 10,746,419 | B2 * | 8/2020 | Sakai | F24F 6/04 |
| 11,179,538 | B2 * | 11/2021 | Kuzelka | B01F 23/20 |
| 11,274,367 | B2 * | 3/2022 | Ono | C23C 16/4485 |
| 2002/0195728 | A1 | 12/2002 | Wooderson | F24F 13/082 261/104 |
| 2003/0192471 | A1 * | 10/2003 | Jurgensen | C23C 16/4481 117/89 |
| 2009/0065066 | A1 * | 3/2009 | Ono | C23C 16/4486 137/13 |
| 2010/0207286 | A1 * | 8/2010 | Jursich | F24F 6/043 261/106 |
| 2010/0313580 | A1 * | 12/2010 | Morioka | B05B 5/057 239/690 |
| 2011/0197816 | A1 * | 8/2011 | Ono | C23C 16/4486 118/726 |
| 2011/0259972 | A1 * | 10/2011 | Rosenthal | A61M 15/06 422/305 |
| 2012/0111554 | A1 * | 5/2012 | Wilson | F24F 11/30 239/23 |
| 2012/0267804 | A1 * | 10/2012 | Rodrigs | F24F 6/04 261/107 |
| 2013/0011308 | A1 * | 1/2013 | Tiwari | C10J 3/845 422/207 |
| 2013/0106004 | A1 * | 5/2013 | Stumphauzer | F24F 6/04 261/127 |
| 2013/0186611 | A1 * | 7/2013 | Schneider | F24F 6/043 236/44 A |
| 2013/0213076 | A1 * | 8/2013 | Gerlach | F24F 13/15 261/104 |
| 2013/0313729 | A1 * | 11/2013 | Sakai | F24F 6/025 261/130 |
| 2015/0153052 | A1 * | 6/2015 | Saito | F24F 11/70 261/130 |
| 2015/0204626 | A1 * | 7/2015 | Martell | F28C 1/14 165/200 |
| 2015/0219346 | A1 * | 8/2015 | Morikawa | F24F 6/04 261/142 |
| 2015/0253046 | A1 * | 9/2015 | Parker | F24F 6/04 62/304 |
| 2016/0007410 | A1 * | 1/2016 | Long | H05B 3/06 219/539 |
| 2016/0040897 | A1 * | 2/2016 | Sakai | F24F 13/08 261/101 |
| 2016/0146483 | A1 * | 5/2016 | Sakai | F24F 6/04 261/26 |
| 2016/0251521 | A1 * | 9/2016 | Izutani | C09D 1/00 261/101 |
| 2017/0211265 | A1 * | 7/2017 | Pasquini | G01F 11/26 |
| 2018/0148836 | A1 * | 5/2018 | Long | C23C 14/54 |
| 2018/0172299 | A1 * | 6/2018 | Conrad | B01F 23/21 |
| 2019/0388930 | A1 * | 12/2019 | Dau | B05B 17/0646 |
| 2020/0217527 | A1 * | 7/2020 | Barlettano | F24F 5/0035 |

FOREIGN PATENT DOCUMENTS

| | | | | |
|---|---|---|---|---|
| EP | 405481 A | * | 1/1991 | ............ B05B 17/04 |
| JP | S61-097063 A | | 5/1986 | |
| JP | S61-125368 U | | 8/1986 | |
| JP | S61125368 | * | 8/1986 | |
| JP | H02-035958 A | | 2/1990 | |
| JP | H07-000883 A | | 1/1995 | |
| JP | 2003302077 A | * | 10/2003 | |
| JP | 2008-196837 A | | 8/2008 | |
| JP | 2009-034576 A | | 2/2009 | |
| JP | 4841683 B1 | | 12/2011 | |
| JP | 5032389 B2 | | 9/2012 | |
| JP | 5289389 B2 | | 9/2013 | |
| JP | 5885653 B2 | | 3/2016 | |
| JP | 2019-138229 A | | 8/2019 | |
| JP | 2020163278 A | * | 10/2020 | |
| KR | 20160038203 | * | 4/2016 | |
| KR | 491008 Y1 | * | 2/2020 | ............ B01D 47/02 |
| KR | 2021016772 A | * | 2/2021 | ............ A61L 9/012 |
| WO | WO-9312266 A1 | * | 6/1993 | ............ C23C 16/18 |
| WO | WO-0058022 A1 | * | 10/2000 | ......... A61M 11/001 |

(56) References Cited

FOREIGN PATENT DOCUMENTS

| WO | WO-2006101767 A2 * | 9/2006 | ................ B01J 7/00 |
| WO | WO-2017100955 A2 * | 6/2017 | .......... F24F 11/0008 |

OTHER PUBLICATIONS

EPO translation of KR20160038203 (Year: 2016).*
Feb. 26, 2019 International Search Report issued in International Patent Application No. PCT/JP2019/001472.
Aug. 18, 2020 International Preliminary Report on Patentability issued in International Patent Application No. PCT/JP2019/001472.

* cited by examiner

LIQUID ATOMIZING APPARATUS

CROSS-REFERENCE TO RELATED APPLICATIONS

This is a US national phase application based on the PCT International Patent Application No. PCT/JP2019/001472 filed on Jan. 18, 2019, and claiming the priority of Japanese Patent Application No. 2018-022654 filed on Feb. 12, 2018, the entire contents of which are herewith incorporated by reference.

TECHNICAL FIELD

The present invention relates to a liquid atomizing apparatus to atomize and release a liquid, such as water.

BACKGROUND ART

There have been used many types of devices configured to atomize a liquid to be used; for example, an air conditioner such as a humidifier, a health and beauty promoting device such as a facial massager and a sauna, a medicament applicator such as a pesticide tool, a medical device such as a chemical solution inhaler, a coating device for applying a coating material or paint in the form of mist. As a method of atomizing a liquid, there have been known for example a method of spraying a pressurized liquid from a nozzle into an atomized form, a method using a rotating body for scattering water contacting thereto by centrifugal force (see Patent Document 1), a method of generating cavitation in a liquid by a ultrasonic vibrator to atomize the liquid.

RELATED ART DOCUMENTS

Patent Documents

Patent Document 1: Japanese Patent No. 5032389

SUMMARY OF INVENTION

Problems to be Solved by the Invention

However, the method disclosed in Patent Document 1 would have to lead to a complex device including a mechanism for rotating the rotating body and others. Further, the method using the ultrasonic vibrator needs for example an electric circuit for driving the ultrasonic vibrator. The method using the nozzle is apt to cause variations in the particle diameter of atomized droplets.

The present invention has been made to address the above problems and has a purpose to provide a liquid atomizing apparatus capable of atomizing a liquid with a simple structure.

Means of Solving the Problems

To achieve the above-mentioned purpose, one aspect of the present invention provides a liquid atomizing apparatus comprising: an atomizing body member made of a porous body having micropores connected in a three-dimensional network, the atomizing body member having a surface including a part serving as a gas pressurized-inflow surface and another part serving as a gas release surface; a liquid supply unit configured to supply a liquid to the atomizing body member, the liquid being to be impregnated into the micropores of the atomizing body member; and a gas supply unit configured to: set a gas pressure on the gas pressurized-inflow surface to be higher than a gas pressure on the gas release surface of the atomizing body member, inject gas into the micropores of the atomizing body member through the gas pressurized-inflow surface, and release a mist of the liquid impregnated in the micropores together with the gas from the gas release surface.

The liquid atomizing apparatus of the present invention can atomize a liquid by injecting gas into the atomizing body member made of a porous body through the gas pressurized-inflow surface and releasing the gas from the atomizing body member through the gas release surface and thereby emitting, from the gas release surface, a mist of the liquid having been impregnated into the atomizing body member (the porous body). Specifically, the liquid atomizing apparatus can atomize a liquid into gas with a simple structure.

The materials of the porous body constituting the atomizing body member may include: porous ceramics made of for example oxide ceramics such as alumina, titania, zirconia, mullite, and silica, nitride ceramics such as silicon nitride, and carbide ceramics such as silicon carbide; and porous glass. Furthermore, the materials of the porous body constituting the atomizing body member also may include: porous metal made of for example stainless steel, titanium, titanium alloy, nickel, nickel alloy, copper alloy, and aluminum; and porous resin made of for example fluororesin such as PTFE, polyethylene, polypropylene, and polymethyl methacrylate resins.

The atomizing body member has a surface including a part serving as a gas pressurized-inflow surface and another part serving as a gas release surface. This atomizing body member is configured in for example a plate-like (flat plate-like, concave, convex, semispherical shell-like, spherical shell-like) shape so that one principal plane serves as a gas pressurized-inflow surface and the other principal plane opposite to the one principal plane in the thickness direction of the atomizing body member serves as a gas release surface. As alternatives, the atomizing body member may be configured in a tubular (rectangular tubular, cylindrical) shape, a bottom-closed tubular (a bottom-closed rectangular tubular, a bottom-closed cylindrical) shape having one end closed with a porous body member or dense material member. In the tubular or bottom-closed tubular atomizing body member, the inner surface is the gas pressurized-inflow surface and the outer surface is the gas release surface, but also they may be reversed.

The liquid to be atomized may include for example water (drinking water, tap water, distilled water, ion-exchange water, pure water, etc.) and further alcohols such as methanol, ethanol, and IPA. This liquid also may include an aqueous solution containing alcohol such as methanol, acid such as hydrochloric acid and acetic acid, alkali such as sodium hydrate, potassium hydrate, sodium hydrogen carbonate (sodium bicarbonate), and ammonia, perfume, and various water-soluble components, various culture solutions. The liquid still further may include organic solvent such as toluene and xylene, oils such as gasoline and kerosene.

The gas to be injected into the atomizing body member through the gas pressurized-inflow surface may include various gases, such as air, hydrogen, nitrogen, oxygen, carbon dioxide, carbon monoxide, methane, and propane.

A portion or site of the surface of the atomizing body member to be supplied with a liquid may be selected, in consideration of a pathway of the gas passing through the micropores from the gas pressurized-inflow surface to the gas release surface, so that the impregnated liquid lies in the pathway. For instance, the liquid may be supplied to a part or whole of the gas release surface, a part or whole of the gas pressurized-inflow surface, or another surface different from the gas release surface and the gas pressurized-inflow surface. Alternatively, a part or whole of the atomizing body member may be immersed once in the liquid to cause the liquid to permeate the micropores of the atomizing body member from the surface in contact with the liquid, and thereafter be pulled out of the liquid.

In the foregoing liquid atomizing apparatus, the liquid supply unit may be a release-surface liquid supply unit configured to supply the liquid to at least a part of the gas release surface.

In the above liquid atomizing apparatus, the release-surface liquid supply unit is configured to supply the liquid to at least a part of the gas release surface. Thus, the liquid atomizing apparatus has only to supply the liquid to be atomized to the gas release surface facing outward, in the atomizing body member, and hence can be configured with a simple structure.

In the foregoing liquid atomizing apparatus, the gas release surface may include a portion on which the liquid supplied from the release-surface liquid supply unit flows and spreads, the portion forming an upward inclined surface facing obliquely upward.

In the above liquid atomizing apparatus, the gas release surface includes a portion or site (hereinafter referred to as a liquid supplied surface) on which the liquid supplied from the release-surface liquid supply unit flows and spreads, forming a liquid film, forms an upward inclined surface. Accordingly, the liquid film of the supplied liquid is caused to spread more quickly in a wider area on the liquid supplied surface of the gas release surface as compared with a configuration that the gas release surface is a horizontal plane. This configuration can facilitate rapid permeation of the liquid from this liquid supplied surface into the micropores of the atomizing body member. Thus, the liquid atomizing apparatus can prevent the liquid from staying on the gas release surface or avoid the liquid from falling off the atomizing body member, resulting in waste, and can appropriately generate a mist of the liquid.

In the foregoing liquid atomizing apparatus, the upward inclined surface may be defined by a normal making an elevation angle of 45° or less.

In the above liquid atomizing apparatus, the normal to the liquid supplied surface (a portion or site of the gas release surface, on which the liquid flows and spreads) which is the upward inclined surface makes an elevation angle of 45° or less, that is, the liquid supplied surface is provided as a steeply inclined surface. Accordingly, the liquid supplied by the release-surface liquid supply unit is particularly caused to flow and spread over a wide area (over the wide liquid supplied surface), so that the liquid quickly permeates into the micropores of the atomizing body member through the liquid supplied surface. This can reliably generate a mist of the liquid.

Alternatively, in the liquid atomizing apparatus initially described, the liquid supply unit may include: a liquid container configured to store the liquid; and a moving mechanism configured to move at least one of the liquid container and the atomizing body member to realize: a contact state where at least a part of the atomizing body member is brought in contact with a stored liquid which is the liquid stored in the liquid container so that the liquid is impregnated into the micropores of the atomizing body member; and a separated state where the atomizing body member is separated from the stored liquid. The gas supply unit may be configured to set the gas pressure on the gas pressurized-inflow surface to be higher than the gas pressure on the gas release surface of the atomizing body member while the moving mechanism realizes the separated state.

In the above liquid atomizing apparatus, the liquid supply unit is configured such that the moving mechanism moves at least one of the liquid container and the atomizing body member to realize the contact state and the separated state and, while the separated state is realized, the gas supply unit is configured to set the gas pressure on the gas pressurized-inflow surface to be higher than the gas pressure on the gas release surface of the atomizing body member. Accordingly, when the contact state is realized and then the separated state is carried out and gas is supplied by the gas supply unit, the liquid atomizing apparatus can release the liquid in a mist form. Thus, alternately realizing the contact state and the separated state enables intermittent generation of a mist.

The configuration for bringing at least a part of the atomizing body member into contact with the stored liquid may include for example a configuration that brings a part or whole of the surface of the atomizing body member into contact with the liquid level of the stored liquid to cause the liquid to be sucked up into the micropores of the atomizing body member through the surface. It may further include another configuration that immerses a part or whole of the atomizing body member into the stored liquid to cause the liquid to permeate the micropores of the atomizing body member from the contacting part of the surface of the atomizing body member with the stored liquid.

MODE FOR CARRYING OUT THE INVENTION

Embodiment 1

Figure 1:
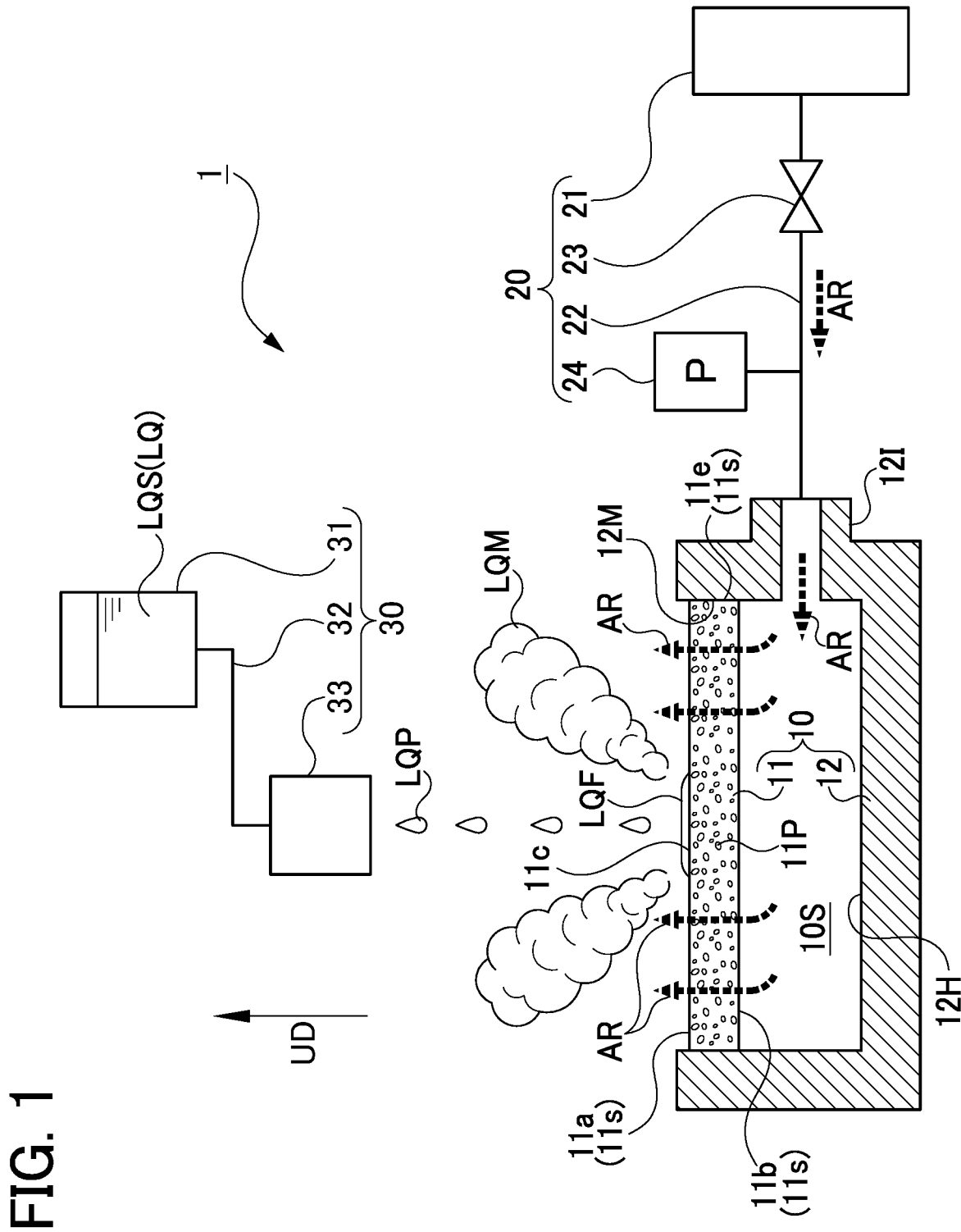
FIG. 1 is an explanatory view showing a configuration of a liquid atomizing apparatus in a first embodiment.

A detailed description of a first embodiment of a liquid atomizing apparatus 1 will now be given referring to FIG. 1. FIG. 1 is an explanatory view schematically showing a configuration of the liquid atomizing apparatus 1 in the first embodiment.

The liquid atomizing apparatus 1 is provided with an atomizing unit 10 configured to generate a mist LQM of a liquid LQ, a gas supply unit 20 configured to supply gas AR to the atomizing unit 10, and a liquid supply unit 30 configured to supply the liquid LQ to an atomizing body member 11 of the atomizing unit 10.

The atomizing unit 10 includes the atomizing body member 11 having a disk-like shape and a holder member 12 holding the atomizing body member 11. The atomizing body member 11 is made of an alumina-based ceramic porous body having micropores 11P connected in a three-dimensional network. The disk-shaped atomizing body member 11 has a surface 11s including one principal plane facing outward (to an upper side UD) serving as a gas release surface 11a and the other principal plane serving as a gas pressurized-inflow surface 11b, the other principal plane being a back surface of of the gas release surface 11a, i.e., opposite to the gas release surface 11a in a thickness direction. This atomizing body member 11 has a thickness of 1.5 mm and micropores 11P having a pore diameter distribution of 0.4 to 2.0 µm and an average pore diameter of 1.3 and has a porosity of 40%. The holder member 12 has a bottom-closed cylindrical shape having a columnar recess 12H including a holding opening 12M located at an upper side thereof. In this holding opening 12M, a side surface 11e of the surface 11s of the atomizing body member 11 is retained. Furthermore, the holder member 12 is provided, on its periphery, with a gas introducing part 121 configured to introduce the gas AR into the holder member 12. In the first embodiment, the atomizing unit 10 is held in such an orientation that the gas release surface 11a of the atomizing body member 11 is horizontal.

The gas AR introduced through the gas introducing part 121 flows in an enclosed space 10S surrounded by the atomizing body member 11 and the recess 12H of the holder member 12. As indicated by arrows in FIG. 1, the gas is then injected into the micropores 11P of the atomizing body member 11 through the gas pressurized-inflow surface 11b of the atomizing body member 11 by a pressure difference between the gas pressurized-inflow surface 11b and the gas release surface 11a of the atomizing body member 11. The gas passes through the micropores 11P and is released to the outside through the gas release surface 11a. This atomizing body member 11 is applied with a critical pressure $\Delta Pc$ of $4\gamma \cos \theta/D$, the critical pressure $\Delta Pc$ being the pressure at which the gas pushes out the liquid LQ having been impregnated in the micropores 11P. Herein, $\gamma$ denotes a surface tension, $\theta$ represents a contact angle of the liquid LQ, D is an average pore diameter of a porous body. The present embodiment uses a porous body having an average pore diameter D of 1.3 µm, and the critical pressure $\Delta Pc$ is 0.16 MPa.

The gas supply unit 20 is configured to supply the gas AR to the gas introducing part 121 of the atomizing unit 10. This gas supply unit 20 includes a gas cylinder 21 for storing the gas AR, a gas pipe 22 for delivering the gas AR from the gas cylinder 21, a valve 23 configured to open and close a flow of the gas AR, and a pressure meter 24 placed downstream of the valve 23 and configured to detect the pressure of gas AR to be supplied to the atomizing unit 10. The valve 23 may be of any valve structure, a manually-operable valve or an electrically-controllable valve such as an electromagnetic valve. In the first embodiment, compressed air is used as the gas AR. Thus, instead of using the gas cylinder 21, another configuration that generates compressed air by use of a compressor or the like and delivers the compressed air to the gas pipe 22 may be adopted.

The liquid supply unit 30 is configured to supply the liquid LQ to the atomizing body member 11 of the atomizing unit 10. This liquid supply unit 30 includes a liquid container 31 for storing a stored liquid LQS (the liquid LQ), a liquid pipe 32 for delivering the liquid LQ and a droplet generating part 33 placed on the upper side UD above the atomizing body member 11 and configured to generate droplets LQP from the liquid LQ that intermittently fall down, toward the gas release surface 11a of the atomizing body member 11. The liquid supply unit 30 in the first embodiment serves as a liquid supply unit (namely, a release-surface liquid supply unit) for supplying the liquid LQ to a part of the gas release surface 11a as described above. In the first embodiment, water is used as the liquid LQ.

While the valve 23 of the gas supply unit 20 is opened, the gas AR is supplied to the atomizing unit 10 at a gas pressure of 0.17 MPa in the pressure meter 24, and the gas AR is released through the gas release surface 11a of the atomizing body member 11, the droplets LQP are dropped from the droplet generating part 33 onto the gas release surface 11a of the atomizing body member 11. The liquid LQ thus forms a circular liquid film LQF on the gas release surface 11a, which spreads onto a part of the gas release surface 11a (this part is referred to as a release-surface liquid supplied surface 11c) and further permeates into the micropores 11P of the atomizing body member 11.

The liquid LQ impregnated in the form of droplets LQP in the micropores 11P is released in the form of mist LQM from the gas release surface 11a together with the gas AR released through the gas release surface 11a as shown in FIG. 1. Accordingly, the droplets LQP are intermittently dropped from the droplet generating part 33 toward the gas release surface 11a of the atomizing body member 11, thereby consecutively causing intermittent generation of mist LQM of the liquid LQ. The size of each droplet LQP caused to fall from the droplet generating part 33 toward the gas release surface 11a (the release-surface liquid supplied surface 11c) and the amount of falling droplets per unit of time may be selected so that a next droplet LQP is supplied at or after the time when all of the falling droplets LQP could be released as the mist LQM through the gas release surface 11a.

In the present embodiment, it was observed that the particle diameter of the mist LQM was distributed in a range of 0.17 to 2.0 µm, the mist LQM whose particle diameter is approximately 1 µm or less, having a mode particle diameter of 0.25 µm and an average particle diameter of 0.35 µm, could be generated at a density of 250 particles/cc (Measuring device: an aerosol spectrometer, WELAS DIGITAL 3000, manufactured by PALAS).

The liquid atomizing apparatus 1 in the first embodiment as described above is configured to inject the gas AR into the atomizing body member 11 made of a porous body through the gas pressurized-inflow surface 11b and release the gas AR out of the atomizing body member 11 through the gas release surface 11a, and thereby emit the mist LQM of the liquid LQ having been impregnated in the atomizing body member 11 from the gas release surface 11a to atomize the liquid LQ. Specifically, the liquid atomizing apparatus 1 can atomize the liquid LQ into the gas AR with a simple structure. In the liquid atomizing apparatus 1 in the first embodiment, furthermore, the liquid supply unit 30 (the droplet generating part 33) is also configured to supply the liquid LQ to the release-surface liquid supplied surface 11c corresponding to a part of the gas release surface 11a. In other words, the liquid atomizing apparatus 1 has only to supply the liquid LQ to be atomized to the gas release surface 11a facing outward of the atomizing body member 11, and thus can be configured with a particularly simple structure.

Embodiment 2

Figure 2:
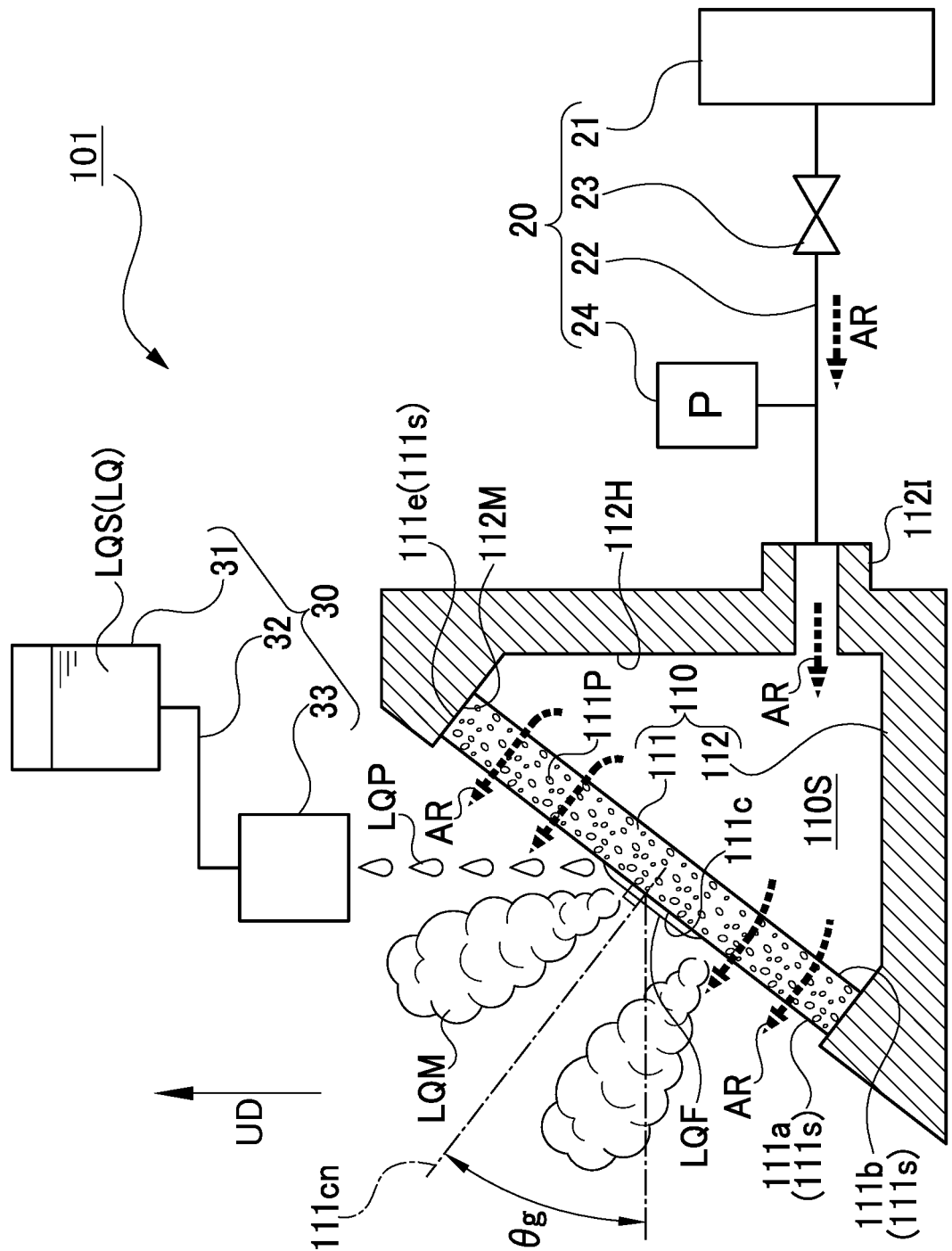
FIG. 2 is an explanatory view showing a configuration of a liquid atomizing apparatus in a second embodiment.

A liquid atomizing apparatus 101 according to a second embodiment will be described with reference to FIG. 2. FIG. 2 is an explanatory view schematically showing a configuration of the liquid atomizing apparatus 101 in the second embodiment. In the liquid atomizing apparatus 1 in the first embodiment, the gas release surface 11a of the atomizing body member 11 is placed horizontally and the droplets LQP are dropped onto this gas release surface 11a. In contrast, in the liquid atomizing apparatus 101 in the second embodiment, differently from the first embodiment, a gas release surface 111a of a plate-like atomizing body member 111 is held obliquely. The following description is therefore given with a focus on the differences from the first embodiment. Similar or identical parts to those in the first embodiment are assigned the same reference signs as those in the first embodiment and their details are omitted or simplified.

The liquid atomizing apparatus 101 in the second embodiment is provided with an atomizing unit 110 configured to generate a mist LQM of a liquid LQ, a gas supply unit 20 configured to supply gas AR to the atomizing unit 110, and a liquid supply unit 30 configured to supply the liquid LQ to the atomizing body member 111 of the atomizing unit 110. The gas supply unit 20 is identical to that in the first embodiment and its details are omitted.

The atomizing unit 110 of the liquid atomizing apparatus 101 includes the atomizing body member 111 having a rectangular plate-like shape and a holder member 112 holding this atomizing body member 111. The atomizing body member 111 is made of an alumina-based ceramic porous body having micropores 111P as with the atomizing body member 11 in the first embodiment. The atomizing body member 111 has a surface 111s including one principal plane facing outward (in an obliquely upper-left direction in the figure) serving as a gas release surface 111a and the other principal plane serving as a gas pressurized-inflow surface 111b, the other principal plane being a back surface of the gas release surface 111a, i.e., opposite to the gas release surface 111a in a thickness direction. This atomizing body member 111 also has a thickness of 1.5 mm and micropores 111P having a pore diameter distribution of 0.4 to 2.0 µm and an average pore diameter of 1.3 and has a porosity of 40%. The holder member 112 has an L-shaped cross-section that encloses a recess 112H having a triangular cross-section. In a holding opening 112M located at an upper-left side in the figure relative to the recess 112H, a side surface 111e of the surface 111s of the atomizing body member 111 is retained. Furthermore, the holder member 112 is provided, on its side, with a gas introducing part 112I configured to introduce the gas AR from the gas supply unit 20 into the holder member 112. In the second embodiment, the atomizing unit 110 is held in such an orientation that the gas release surface 111a of the atomizing body member 111 obliquely faces to the upper-left in the figure.

In the atomizing unit 110 in the second embodiment, as in the first embodiment, the gas AR introduced through the gas introducing part 112I flows in an enclosed space 110S surrounded by the atomizing body member 111 and the recess 112H of the holder member 112. As indicated by arrows in FIG. 2, the gas is then injected into the micropores 111P of the atomizing body member 111 through the gas pressurized-inflow surface 111b of the atomizing body member 111 by a pressure difference between the gas pressurized-inflow surface 111b (the inner surface) of the atomizing body member 111 and the gas release surface 111a (the outer surface). The gas passes through the micropores 111P and is released to the outside through the gas release surface 111a.

The liquid supply unit 30 is configured to supply the liquid LQ to the atomizing body member 111 of the atomizing unit 110. This liquid supply unit 30 includes, as in the first embodiment, a liquid container 31 for storing a stored liquid LQS (the liquid LQ), a liquid pipe 32 for delivering the liquid LQ, and additionally a droplet generating part 33 placed on an upper side UD above the atomizing body member 111 and configured to cause the liquid LQ to intermittently fall in drops, generating droplets LQP, toward the gas release surface 111a of the atomizing body member 111. The liquid supply unit 30 in the second embodiment also serves as a release-surface liquid supply unit for supplying the liquid LQ to a part of the gas release surface 111a. In the second embodiment, water is used as the liquid LQ.

While the valve 23 of the gas supply unit 20 is opened, the gas AR is supplied to the atomizing unit 110 at a gas pressure of 0.17 MPa in the pressure meter 24, and the gas AR is released through the gas release surface 111a of the atomizing body member 111, an appropriate amount of the liquid LQ is supplied in the form of droplets LQP from the droplet generating part 33 onto the gas release surface 111a of the atomizing body member 111. The liquid LQ thus forms a liquid film LQF on the gas release surface 111a, which spreads onto a part of the gas release surface 111a (this part is referred to as a release-surface liquid supplied surface 111c) and further permeates into the micropores 111P of the atomizing body member 111. Concurrently, a mist LQM of the liquid LQ is released together with the gas AR from the atomizing body member 111 through the gas release surface 111a.

In the second embodiment, particularly, the gas release surface 111a, i.e., the release-surface liquid supplied surface 111c, obliquely faces to the upper left in the figure. To be concrete, the atomizing body member 111 is placed in a steeply-inclined orientation so that the release-surface liquid supplied surface 111c is defined by a normal 111cn making an elevation angle θg of 45° or less, specifically, an elevation angle θg of 30° (θg=30°) in the second embodiment. Accordingly, the liquid LQ supplied in the form of droplets LQP to the gas release surface 111a forms an elliptic liquid film LQF extending downward on the gas release surface 111a. This liquid film LQF is caused to rapidly flow and spread over a wider range (the release-surface liquid supplied surface 111c) as compared with the configuration that the gas release surface is placed in a horizontal orientation (see the first embodiment). In the second embodiment therefore, the liquid LQ is allowed to be impregnated into the micropores 111P of the atomizing body member 111 in a wider area.

The amount of the liquid LQ to be supplied per unit of time to the gas release surface 111a (the release-surface liquid supplied surface 111c) from the droplet generating part 33 may be selected as the amount well-balanced with the amount of supplied liquid LQ releasable as mist LQM through the gas release surface 111a. This makes it possible to avoid part of the supplied liquid LQ from dropping out of the atomizing body member 111 without permeating into the micropores 111P of the atomizing body member 111.

The liquid atomizing apparatus 101 in the second embodiment is also configured to inject the gas AR into the atomizing body member 111 made of a porous body through the gas pressurized-inflow surface 111b and release the gas AR out of the atomizing body member 111 through the gas release surface 111a, and thereby emit, from the gas release surface 111a, the mist LQM of the liquid LQ having been impregnated in the atomizing body member 111 to atomize the liquid LQ. Specifically, the liquid atomizing apparatus 101 can atomize the liquid LQ into the gas AR with a simple structure. In the liquid atomizing apparatus 101 in the second embodiment, furthermore, the liquid supply unit 30 (the droplet generating part 33) is also configured to supply the liquid LQ to the release-surface liquid supplied surface 111c corresponding to a part of the gas release surface 111a. In other words, the liquid atomizing apparatus 101 has only to supply the liquid LQ to be atomized to the gas release surface 111a facing obliquely upward of the atomizing body member 111, and thus can be configured with a particularly simple structure.

In the liquid atomizing apparatus 101 in the second embodiment, the release-surface liquid supplied surface 111c of the gas release surface 111a forms an upward inclined surface, on which the liquid LQ supplied onto the gas release surface 111a by the liquid supply unit 30 is allowed to flow and spread in the form of a liquid film LQF. As compared with the configuration that the gas release surface 111a is placed horizontally, therefore, the liquid film LQF of the supplied liquid LQ is caused to quickly flow and spread over a wider range on the gas release surface 111a. The liquid LQ is allowed to be impregnated rapidly into the micropores 111P of the atomizing body member 111 through the release-surface liquid supplied surface 111c. This can prevent the liquid LQ from staying on the gas release surface 111a, and prevent the liquid LQ from falling off the atomizing body member 111 through the gas release surface 111a, resulting in waste, and thus appropriately generate the mist LQM from the liquid LQ.

In the liquid atomizing apparatus 101, especially, the normal 111cn to the release-surface liquid supplied surface 111c (a portion or site of the gas release surface 111a, on which the liquid flows) which is an upward inclined surface makes an elevation angle θg of 45° or less, concretely, an elevation angle θg of 30°. Specifically, the release-surface liquid supplied surface 111c forms a steeply-inclined surface. Accordingly, the liquid LQ supplied by the liquid supply unit 30 is particularly caused to flow and spread over a wide range (the wide release-surface liquid supplied surface 111c), so that the liquid LQ quickly permeates into the micropores 111P of the atomizing body member 111 through the release-surface liquid supplied surface 111c, thereby reliably atomizing the liquid LQ.

Embodiment 3

Figure 3:
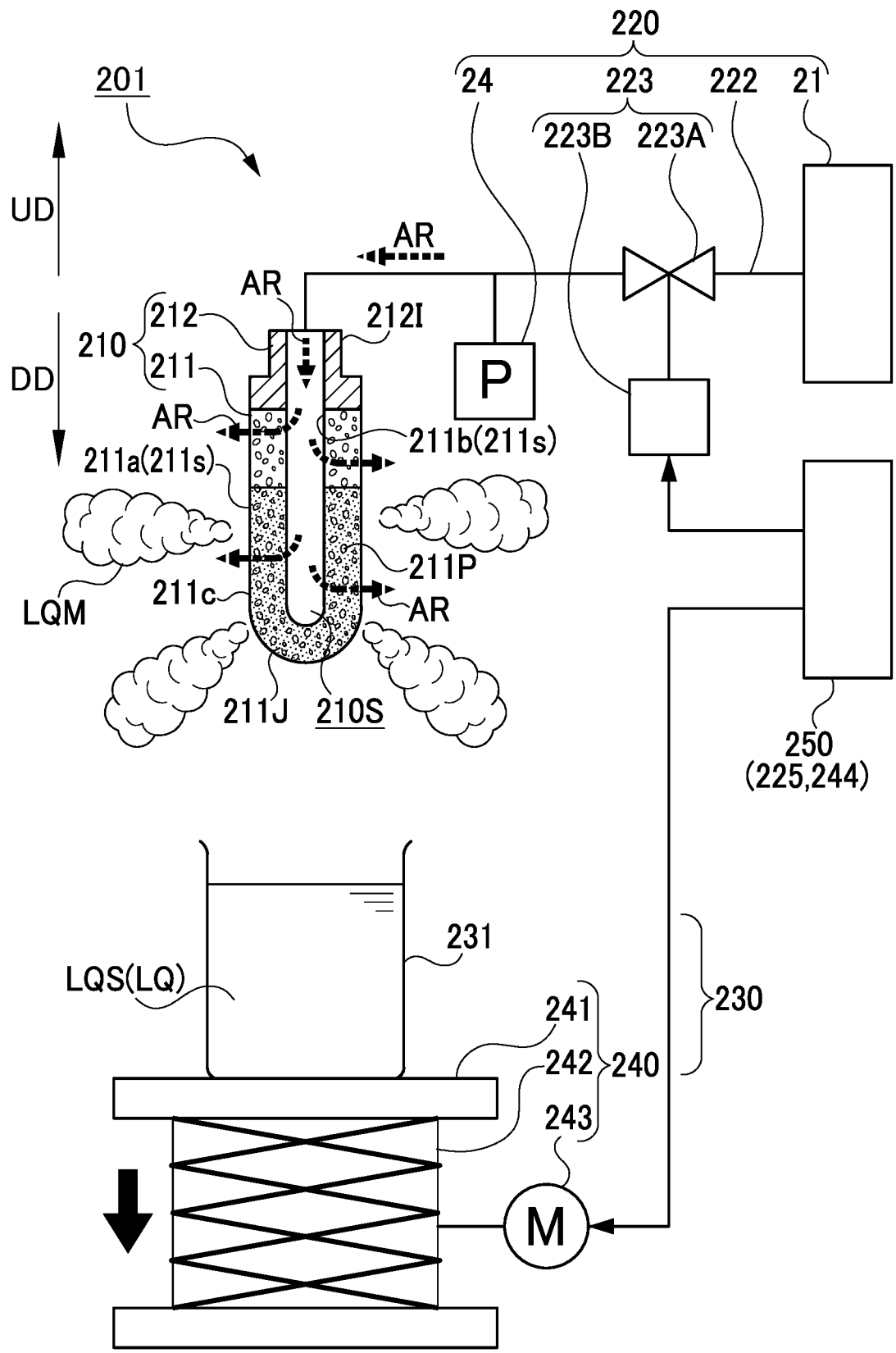
FIG. 3 is an explanatory view showing a configuration of a liquid atomizing apparatus in a third embodiment in which a separated state is realized by a moving mechanism.
Figure 4:
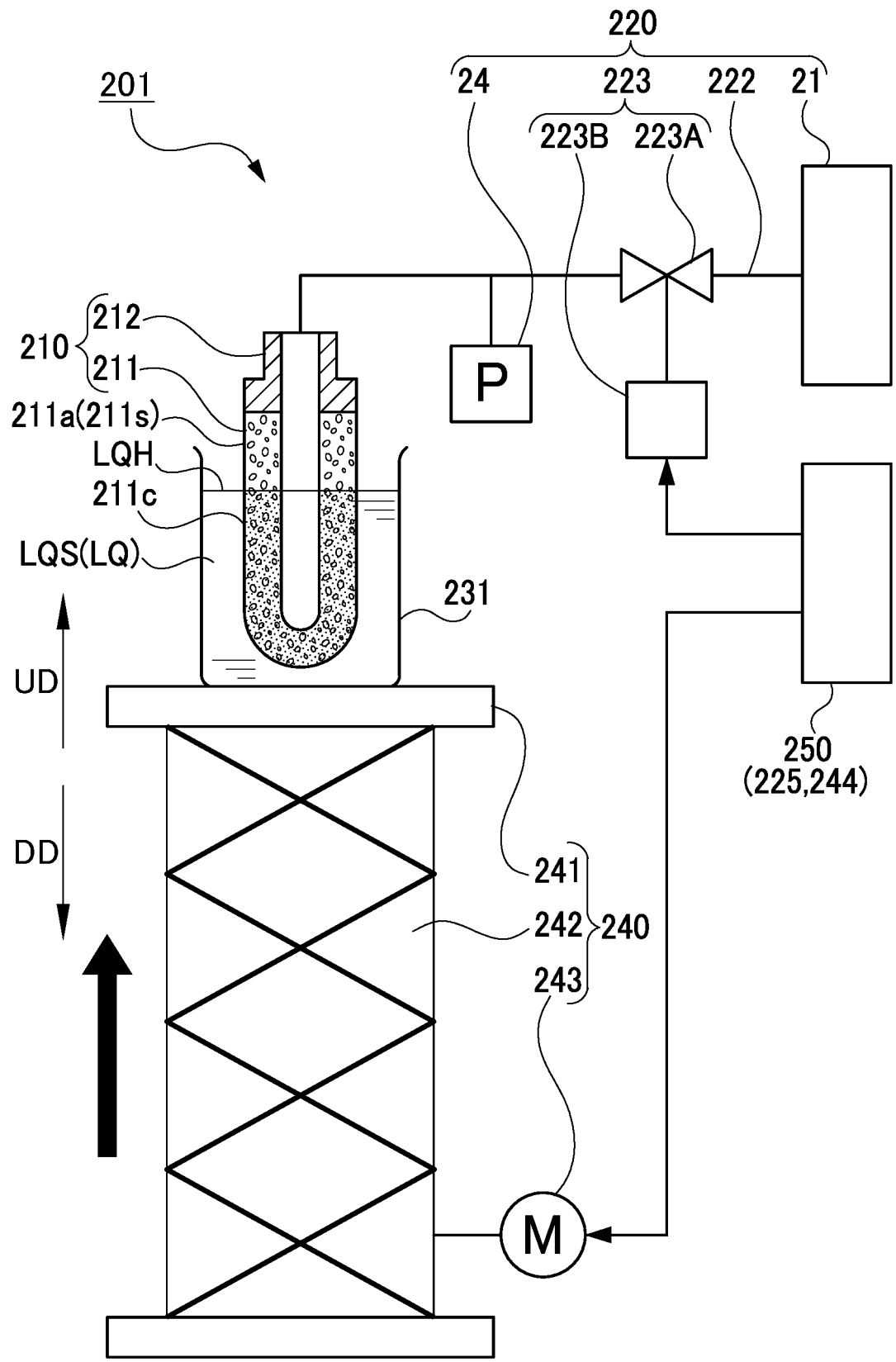
FIG. 4 is an explanatory view showing a configuration of the liquid atomizing apparatus in the third embodiment in which a contact state is realized by the moving mechanism.

A liquid atomizing apparatus 201 according to a third embodiment will be described with reference to FIGS. 3 and 4. FIGS. 3 and 4 are explanatory views schematically showing a configuration of the liquid atomizing apparatus 201 in the third embodiment. Specifically, FIG. 3 is an explanatory diagram showing the configuration that a separated state described later is realized by a moving mechanism 240 and the gas AR is supplied to the atomizing unit 210 to generate a mist LQM of a liquid LQ from the atomizing body member 211. On the other hand, FIG. 4 is an explanatory diagram showing the configuration that a contact state described later is realized by the moving mechanism 240 and the atomizing body member 211 is immersed in a stored liquid LQS to impregnate the atomizing body member 211 with the liquid.

The liquid atomizing apparatus 201 in the third embodiment is provided with an atomizing unit 210 configured to generate a mist LQM of a liquid LQ, a gas supply unit 220 configured to supply gas AR to the atomizing unit 210, and a liquid supply unit 230 configured to supply the liquid LQ to the atomizing body member 211 of the atomizing unit 210.

The atomizing unit 210 of the liquid atomizing apparatus 201 includes an atomizing body member 211 and a holder member 212 holding this atomizing body member 211. The atomizing body member 211 has a bottom-closed cylindrical shape having a U-shaped cross-section with a distal end (a lower end in the figure) closed in a semi-spherical shape. The atomizing body member 211 is made of an alumina-based ceramic porous body having micropores 211P as with the atomizing body member 11 in the first embodiment and the atomizing body member 111 in the second embodiment.

The atomizing body member 211 has a surface 211s including an outer surface facing outward serving as a gas release surface 211a and an inner surface facing inward serving as a gas pressurized-inflow surface 211b, which is a back surface of the gas release surface 211a, i.e., opposite to the outer surface in a thickness direction. This atomizing body member 211 has a thickness of 1.5 mm and micropores 211P having a pore diameter distribution of 0.4 to 2.0 μm and an average pore diameter of 1.3 μm, and has a porosity of 40%. The holder member 212 has a ring shape and is configured to hold an open end (an upper end in the figure) of the atomizing body member 211. In the upper end of the holder member 212, a gas introducing part 212I is provided to introduce gas AR from the gas supply unit 220. In the third embodiment, a lower part of the atomizing body member 211 is assumed as a liquid impregnated part 211J in which the liquid LQ is to be impregnated.

The gas AR introduced through the gas introducing part 212I flows in an enclosed space 210S in the atomizing body member 211 and then injected, as indicated by arrows in FIG. 3, into the micropores 211P of the atomizing body member 211 through the gas pressurized-inflow surface 211b of the atomizing body member 211 by a pressure difference between the gas pressurized-inflow surface 211b (the inner surface) and the gas release surface 211a (the outer surface) of the atomizing body member 211. The gas AR passes through the micropores 211P and is then released to the outside through the gas release surface 211a.

The gas supply unit 220 is configured to supply the gas AR to the gas introducing part 212I of the atomizing unit 210. This gas supply unit 220 includes a gas cylinder 21 for storing the gas AR, a gas pipe 222 for delivering the gas AR from the gas cylinder 21, a valve 223 configured to open and close a flow of the gas AR, and a pressure meter 24 placed downstream of the valve 223 and configured to detect the pressure of gas AR to be supplied to the atomizing unit 210. The valve 223 includes an electromagnetic valve 223A configured to open and close a flow of the gas AR flowing through the gas pipe 222 and a valve driving circuit 223B configured to drive the electromagnetic valve 223A to open and close. Furthermore, the valve driving circuit 223B of the valve 223 is electrically controlled by a controller 250 including a sequencer. This controller 250 operates as a valve control part 225 and constitutes a part of the gas supply unit 220. In the third embodiment, compressed air is also used as the gas AR. Thus, instead of using the gas cylinder 21, as in the first and second embodiments, another configuration that generates compressed air by use of a compressor or the like and delivers the compressed air to the gas pipe 222 may be adopted.

The liquid supply unit 230 is configured to supply the liquid LQ to the liquid impregnated part 211J of the atomizing body member 211. This liquid supply unit 230 includes a liquid container 231 for storing a stored liquid LQS and a moving mechanism 240 configured to move the liquid container 231 to an upper side UD and to a lower side DD.

The liquid container 231 has a shape that is open on the upper side UD and configured to hold the stored liquid LQS. The moving mechanism 240 includes a holding table part 241 on which the liquid container 231 is mounted and held, a lift part 242 configured to be extendable and contractable to movably support the liquid container 231 and the holding table part 241 to the upper side UD and the lower side DD, and a drive motor 243 configured to drive the lift part 242 to move the holding table part 241 together with the liquid container 231. The drive motor 243 is electrically controlled by the controller 250 including a sequencer. This controller 250 operates as a moving mechanism control part 244 and constitutes a part of the liquid supply unit 230.

In the liquid atomizing apparatus 201, firstly, the controller 250 (the valve control part 225) drives the valve driving circuit 223B to close the electromagnetic valve 223A to thereby shut off supply of the gas AR to the atomizing unit 210. In addition, the controller 250 (the moving mechanism control part 244) drives the driving motor 243 to extend the lift part 242, thereby lifting the liquid container 231 to the upper side UD, so that a part of the atomizing body member 211 is immersed into the stored liquid LQS in the liquid container 231 (the contact state) as shown in FIG. 4. In this contact state, a part of the gas release surface 211a which is the outer surface of the atomizing body member 211, that is, a release-surface liquid supplied surface 211c located on a lower side DD than the liquid level LQH, contacts with the stored liquid LQS (the liquid LQ). Accordingly, in the liquid impregnated part 211J corresponding to a lower part of the atomizing body member 211, the liquid LQ permeates into the micropores 211P. The liquid supply unit 230 in the third embodiment also serves as a release-surface liquid supply unit for supplying the liquid LQ to the release-surface liquid supplied surface 211c which is the part of the gas release surface 211a. In the third embodiment, water is also used as the liquid LQ.

Subsequently, the controller 250 (the moving mechanism control part 244) drives the drive motor 243 to contract the lift part 242, thereby moving the liquid container 231 to the lower side DD, so that the atomizing body member 211 is separated (i.e., in a separated state) from the stored liquid LQS in the liquid container 231. In addition, the controller 250 (the valve control part 225) drives the valve driving circuit 223B to open the electromagnetic valve to supply the air AR to the atomizing unit 210 at a gas pressure of 0.17 MPa in the pressure meter 24. Accordingly, the gas pressurized-inflow surface 211b is subjected to a higher gas pressure than the gas release surface 211a of the atomizing body member 211, thereby forcing the gas AR to emerge from the gas release surface 211a and also release the mist LQM of the liquid LQ together with the gas AR from the liquid impregnated part 211J of the atomizing body member 211.

The liquid atomizing apparatus 201 in the third embodiment described as above is configured to inject the gas AR into the atomizing body member 211 made of a porous body through the gas pressurized-inflow surface 211b and release the gas AR out of the atomizing body member 211 through the gas release surface 211a, and thereby emit, from the gas release surface 211a, the mist LQM of the liquid LQ having been impregnated in advance in the liquid impregnated part 211J of the atomizing body member 211 to atomize the liquid LQ. Specifically, the liquid atomizing apparatus 201 can atomize the liquid LQ into the gas AR with a simple structure. In the liquid atomizing apparatus 201 in the third embodiment, furthermore, the liquid supply unit 230 (the liquid container 231) is also configured to supply the liquid LQ to the release-surface liquid supplied surface 211c corresponding to a part of the gas release surface 211a. In other words, the liquid atomizing apparatus 201 has only to supply the liquid LQ to be atomized to the release-surface liquid supplied surface 211c that is the outer surface of the atomizing body member 211. The liquid atomizing apparatus 201 can be configured with a particularly simple structure.

In this liquid atomizing apparatus 201, moreover, the liquid supply unit 230 is configured such that the moving mechanism 240 moves at least one of the liquid container 231 and the atomizing body member 211 (the liquid container 231 in the third embodiment) to realize the contact state and the separated state and, while the separated state is being realized, the gas supply unit 220 is configured to set the gas pressure on the gas pressurized-inflow surface 211b of the atomizing body member 211 to be higher than on the gas release surface 211a.

Accordingly, when the contact state is realized and then the separated state is carried out and the gas AR is supplied by the gas supply unit 220, the liquid atomizing apparatus 201 can release the mist LQM of the liquid LQ. Thus, the liquid atomizing apparatus 201 can intermittently generate the mist LQM with a simple structure capable of alternately realizing the contact state and the separated state.

In the third embodiment, a part of the atomizing body member 211 is immersed in the stored liquid LQS to impregnate the liquid LQ into the micropores 211P of the atomizing body member 211 through the release-surface liquid supplied surface 211c which is a contacting part of the surface 211s of the atomizing body member 211 with the stored liquid LQS.

As an alternative, the whole atomizing body member 211 may be immersed in the stored liquid LQS. Further, another alternative may be configured to bring only a lower end portion of the gas release surface 211a which is the outer surface of the atomizing body member 211 into contact with the liquid level of the stored liquid LQS without immersing the atomizing body member 211 into the stored liquid LQS, so that the liquid LQ is sucked up into the micropores 211P of the atomizing body member 211.

The present invention is described as above in the first to third embodiments, but the present invention is not limited to the foregoing first to third embodiments and may be embodied in other specific forms without departing from the essential characteristics thereof.

In the first embodiment, the atomizing unit 10 is configured such that the gas release surface 11a is a horizontal plane facing upward, so that a part of the gas release surface 11a onto which the droplets LQP fall down from the upper side UD is used as the release-surface liquid supplied surface (the liquid supplied surface) 11c through which the liquid LQ is supplied to the atomizing body member 11. As an alternative, a part of the gas pressurized-inflow surface, not of the gas release surface, may be configured as the liquid supplied surface. For instance, the gas release surface may be a downward-facing surface, so that the liquid LQ falls in drops onto a part of the upward-facing gas pressurized-inflow surface, thereby enabling the mist LQM of the liquid LQ to be released downward together with the gas AR.

REFERENCE SIGNS LIST 1, 101, 201 Liquid atomizing apparatus
10, 110, 210 Atomizing unit
11, 111, 211 Atomizing body member
11s, 111s, 211s Surface (of Atomizing body member)
11a, 111a, 211a Gas release surface
11b, 111b, 211b Gas pressurized-inflow surface
11c, 111c, 211c Release-surface liquid supplied surface (Liquid supplied surface)
111cn Normal (to Liquid supplied surface)
θg Elevation angle (formed by Normal to Liquid supplied surface)
11e, 111e Side surface (of Atomizing body member)
11P, 111P, 211P Micropore 211J Liquid impregnated part (of Atomizing body member)
20, 220 Gas supply unit
30, 230 Liquid supply unit (Release-surface liquid supply unit, Liquid supply unit)
31, 231 Liquid container
33 Droplet generating part
240 Moving mechanism
UD Upper side
DD Lower side
AR Gas
LQ Liquid
LQP Droplet
LQF Liquid film
LQM Mist (of Liquid)
LQS Stored liquid (stored in Liquid container)

The invention claimed is:

1. A liquid atomizing apparatus comprising:
an atomizing body made of a porous material that is porous ceramics, porous glass, porous metal, or porous resin and has micropores connected in a three-dimensional network, the atomizing body having a gas pressurized-inflow surface and a gas release surface;
a holder member that holds the atomizing body, wherein an enclosed space is surrounded by, and internal to, a combination of the holder member and the gas pressurized-inflow surface;
a liquid supply configured to supply droplets of a liquid to the atomizing body to be impregnated into the micropores of the atomizing body; and
a gas supply configured to:
supply gas to the enclosed space so that a gas pressure on the gas pressurized-inflow surface is higher than a gas pressure on the gas release surface of the atomizing body,
inject the gas into the micropores of the atomizing body through the gas pressurized-inflow surface, and
release a mist of the liquid impregnated in the micropores together with the gas from the gas release surface,
wherein
the gas release surface includes a portion on which the liquid supplied from the liquid supply flows and spreads, the portion forming an upward inclined surface facing obliquely upward.

2. The liquid atomizing apparatus set forth in claim 1, wherein the liquid supply is configured to supply the liquid to at least a part of the gas release surface.

3. The liquid atomizing apparatus set forth in claim 1, wherein the upward inclined surface is defined by a normal making an elevation angle of 45° or less.

4. The liquid atomizing apparatus set forth in claim 1, wherein the gas supply is configured to supply the gas to the enclosed space so that the gas pressure is a positive pressure on the gas pressurized-inflow surface.

* * * * *